United States Patent
Iwata

(10) Patent No.: US 9,943,635 B2
(45) Date of Patent: Apr. 17, 2018

(54) EXTRACORPOREAL CIRCULATION DEVICE AND CONTROL METHOD

(75) Inventor: Takeharu Iwata, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 223 days.

(21) Appl. No.: 14/422,484

(22) PCT Filed: Sep. 5, 2012

(86) PCT No.: PCT/JP2012/005611
§ 371 (c)(1),
(2), (4) Date: Mar. 30, 2015

(87) PCT Pub. No.: WO2014/037971
PCT Pub. Date: Mar. 13, 2014

(65) Prior Publication Data
US 2015/0202358 A1 Jul. 23, 2015

(51) Int. Cl.
*A61M 37/00* (2006.01)
*A61M 1/36* (2006.01)
*A61M 1/10* (2006.01)

(52) U.S. Cl.
CPC ........ *A61M 1/3621* (2013.01); *A61M 1/3644* (2014.02); *A61M 1/3666* (2013.01); *A61M 1/3667* (2014.02); *A61M 1/101* (2013.01); *A61M 1/1006* (2014.02); *A61M 1/1086* (2013.01); *A61M 1/3643* (2013.01); *A61M 2205/17* (2013.01); *A61M 2205/3334* (2013.01)

(58) Field of Classification Search
CPC .............. A61M 1/3621; A61M 1/3667; A61M 1/3666; A61M 1/1006; A61M 1/3643
See application file for complete search history.

(56) References Cited

U.S. PATENT DOCUMENTS

| 6,123,726 A * | 9/2000 | Mori ...................... A61M 1/101 600/17 |
| 6,808,508 B1 * | 10/2004 | Zafirelis ................ A61M 1/101 604/131 |
| 2007/0055908 A1 | 3/2007 | Kubo et al. |
| 2011/0015732 A1 | 1/2011 | Kanebako |

FOREIGN PATENT DOCUMENTS

| JP | 2007014504 | 1/2007 |
| WO | WO2010065398 A1 | 6/2010 |

* cited by examiner

Primary Examiner — Leslie Deak
(74) Attorney, Agent, or Firm — MacMillan, Sobanski & Todd, LLC

(57) ABSTRACT

An extracorporeal circulation device having high safety without increases in the circuit scale and the power consumption includes a main control unit responsible for control of a motor drive circuit so as to yield a blood flow rate per unit time set by a user. The motor drive circuit applies a drive signal corresponding to the set blood flow rate to a motor. A sub-control unit configured by a field programmable gate array (FPGA) detects the drive signal applied to the motor and monitors whether or not the drive signal falls within an allowable range corresponding to the set blood flow rate. If the drive signal outside the allowable range is applied, the main control unit is deemed to be in an abnormal state and the main control unit is completely stopped. Then, the sub-control unit takes over the subsequent processing.

3 Claims, 4 Drawing Sheets

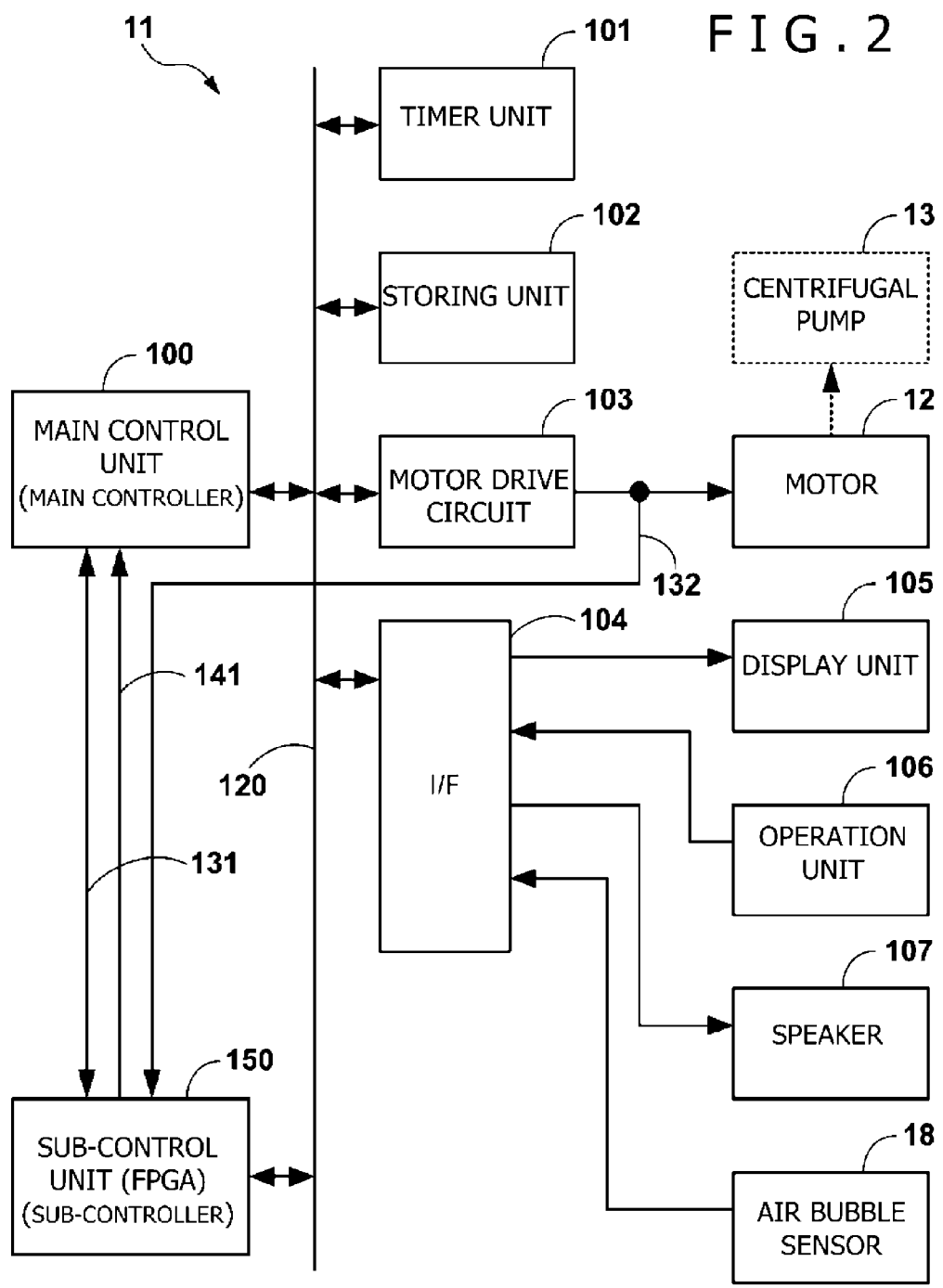

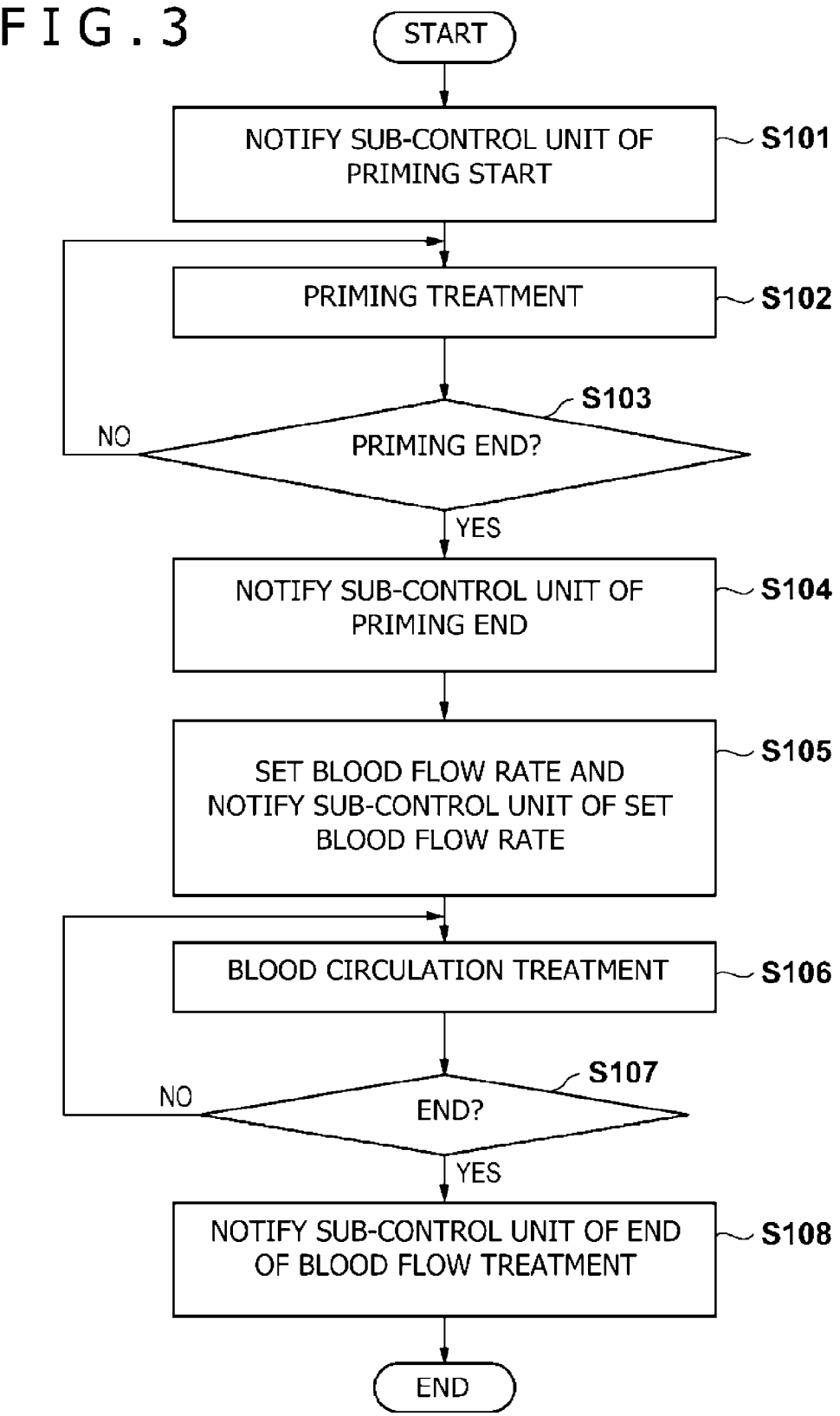

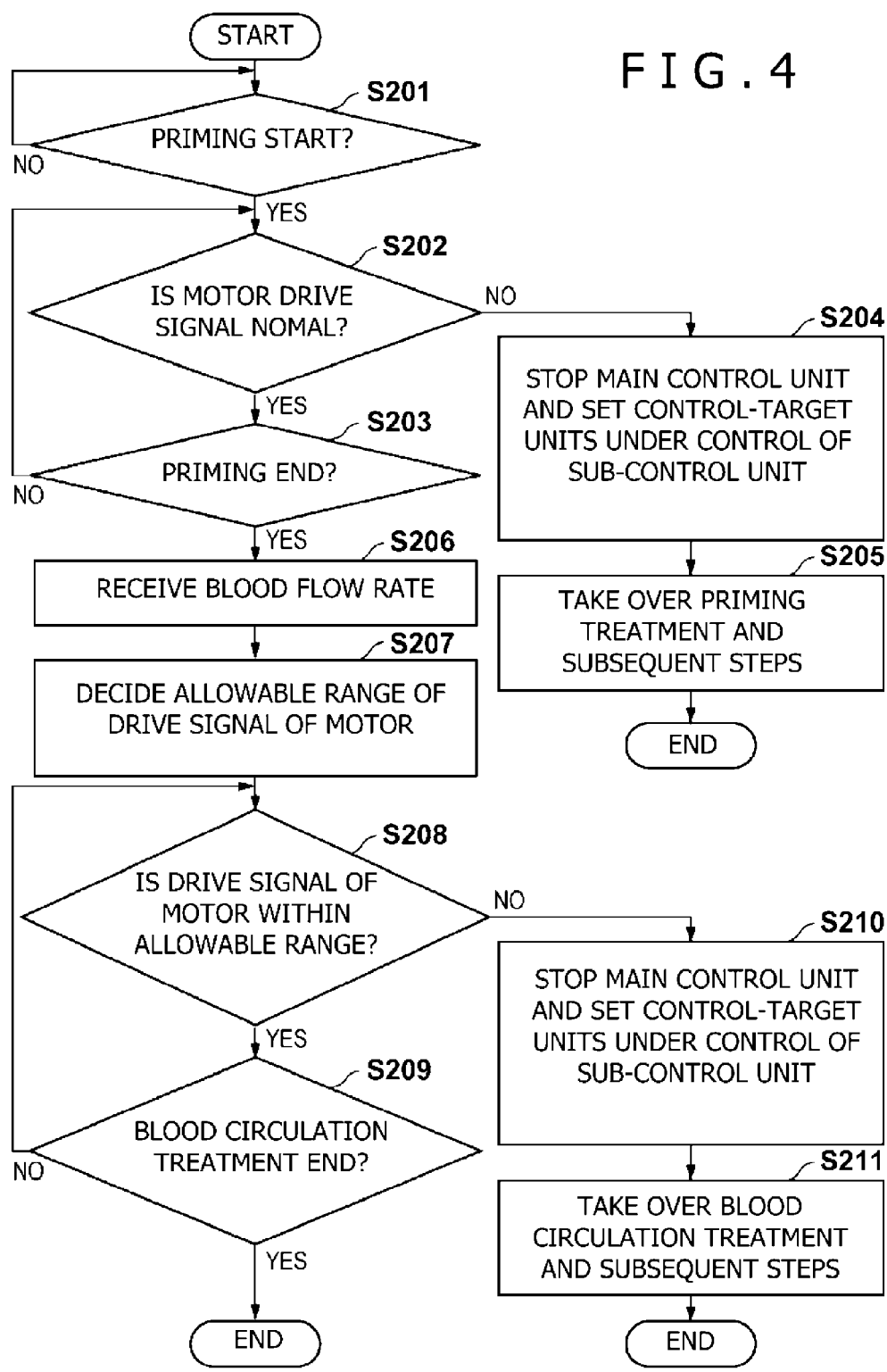

EXTRACORPOREAL CIRCULATION DEVICE AND CONTROL METHOD

TECHNICAL FIELD

The present invention relates to an extracorporeal circulation device and a control method thereof.

BACKGROUND ART

Conventionally, as a representative one of extracorporeal circulation devices, a cardiopulmonary assist device used for a cardiopulmonary assist is known. Such a device is provided with a blood extracorporeal circulation circuit composed of an oxygenator, centrifugal artificial heart (centrifugal pump), controller, oxygen supply source (oxygen tank), and so forth (see, e.g., Japanese patent 4839030).

The cardiopulmonary assist device functions in place of the heart and lung of a patient and is required to have high safety so that it may be prevented from falling into a situation in which it stops in an operation.

One method for ensuring the safety is providing a controller for controlling the respective units configuring the circulation circuit with a duplicated structure with main controller and sub-controller. This is because the sub-controller continues control even if the main controller stops due to any cause. To determine whether or not the main controller is in the stop state, the sub-controller transmits a signal to the main controller at adequate timing and makes the determination based on whether or not a response signal thereof can be received from the main controller. That is, the sub-controller determines that the main controller is in the stop state if the response signal cannot be received within a predetermined time.

As described above, doubling the controller allows construction of a safer system. However, on the other hand, there is a problem that the circuit scale becomes more complicated and increases in the device size and the power consumption are caused.

Furthermore, particularly in the case of artificial heart and lung, during an operation, it is important that the blood flows with an amount of fluid matching the amount per unit time as commanded by a doctor or a person performing the operation. Therefore, even if the main controller issues an erroneous control signal to a drive unit for the centrifugal pump due to any cause, this has not been detected by the prior art as an abnormality.

SUMMARY OF THE INVENTION

The present invention is made in view of the above-described problems and intends to provide an extracorporeal circulation device having high safety while suppressing increases in both the circuit scale and the power consumption, and a control method thereof.

To solve the above-described problems, an extracorporeal circulation device of the present invention has the following condition. Specifically, the extracorporeal circulation device is an extracorporeal circulation device that extracorporeally circulates blood of a subject by using a circulation circuit, and has:

a main control unit that is responsible for control of the extracorporeal circulation device and a sub-control unit that is configured by an FPGA (Field-Programmable Gate Array) and takes over processing relating to extracorporeal circulation in place of the main control unit if the main control unit falls into an abnormal state, wherein the sub-control unit has:

monitoring means that monitors a drive signal applied to a motor of a pump for performing the extracorporeal circulation of the blood, determining means that determines whether the main control unit is in a normal state or is in an abnormal state by determining whether or not the drive signal falls within an allowable range for yielding a set amount of fluid sending per unit time during monitoring by the monitoring means, and treatment means that takes over and handles treatment relating to blood circulation in place of the main control unit if it is determined that the main control unit is in an abnormal state by the determining means.

Advantageous Effects

According to the present invention, it becomes possible to provide an extracorporeal circulation device having high safety while suppressing increases in both the circuit scale and the power consumption.

Other characteristics and advantages of the present invention will become apparent based on the following description with reference to the accompanying drawings. Note that the same or similar configuration is given the same reference numeral in the accompanying drawings.

BRIEF DESCRIPTION OF DRAWINGS

Accompanying drawings are included in the specification and configure part thereof, and are used to show embodiments of the present invention and explain the principle of the present invention together with description of the embodiments.

FIG. 2 is a block configuration diagram of a control device 11.

FIG. 3 is a flowchart showing the processing procedure of a main controller in the control device 11.

FIG. 4 is a flowchart showing the processing procedure of a sub-controller in the control device 11.

DETAILED DESCRIPTION OF PREFERRED EMBODIMENTS

1. Overall Configuration of Extracorporeal Circulation Device

Figure 1A:
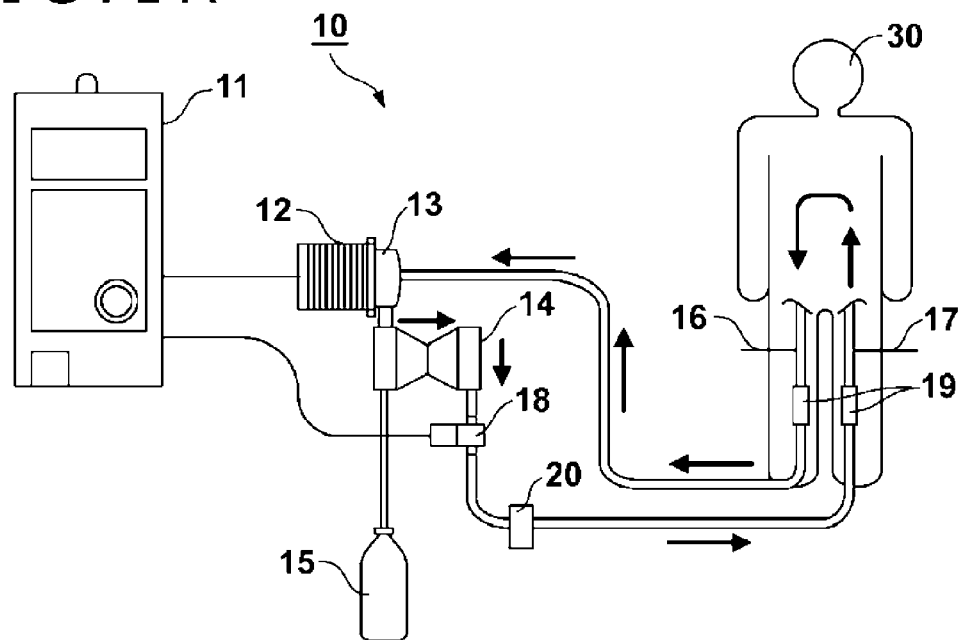
FIG. 1A is a diagram showing one example of the overall configuration of an extracorporeal circulation device 10 according to a first embodiment of the present invention.
Figure 1B:
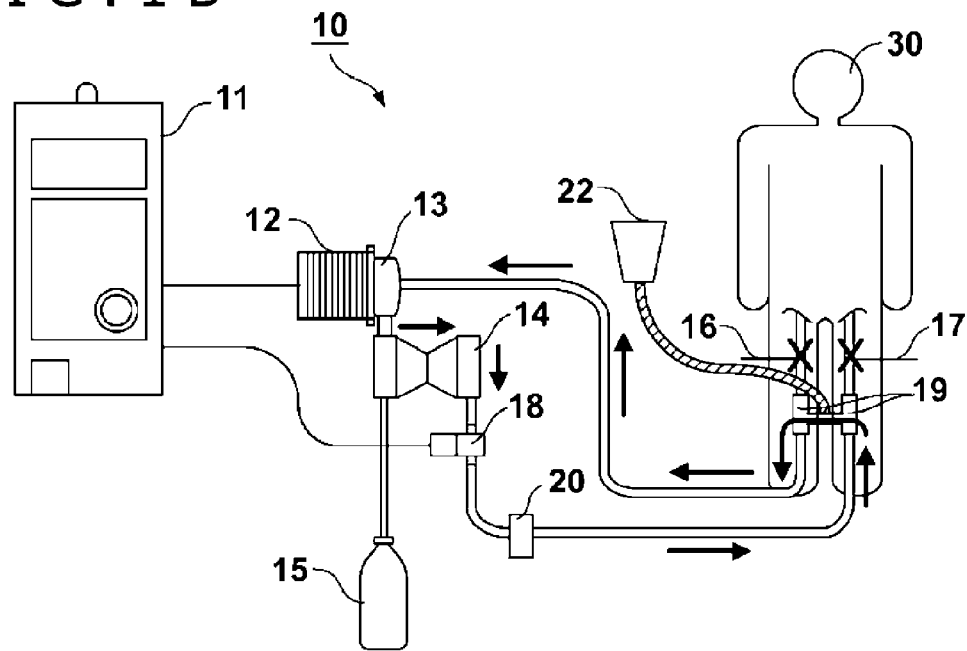
FIG. 1B is a diagram showing one example of the overall configuration of the extracorporeal circulation device 10 according to the first embodiment of the present invention.

FIGS. 1A and 1B are diagrams showing one example of the overall configuration of an extracorporeal circulation device 10 according to a first embodiment of the present invention.

The extracorporeal circulation device 10 carries out cardiopulmonary assist operation (extracorporeal circulation, assisted circulation) used for performing a procedure called PCPS (percutaneous cardiopulmonary support). The extracorporeal circulation device 10 has a blood extracorporeal circulation circuit (hereinafter, referred to as circulation circuit) shown by arrows in the diagrams. In the extracorporeal circulation device 10, after priming operation is carried out, the blood of a subject 30 is extracorporeally circulated by using this circulation circuit.

Here, the priming operation refers to operation of circulating a priming solution (e.g. physiological saline) in the circulation circuit in a state in which the circulation circuit is sufficiently filled with the priming solution to remove air bubbles in this circuit.

The extracorporeal circulation device 10 is provided with a control device 11, a motor 12, a centrifugal pump 13 driven by this motor 12, an oxygenator 14, an oxygen supply source 15, a catheter (venous side) 16, a catheter (arterial side) 17, an air bubble sensor 18, branching lines 19, and a blood filter 20. Note that these respective components are connected by tubes having flexibility or the like and the lumens of these tubes form flow paths of the blood.

The catheter (arterial side) 17 sends the blood toward the inside of the body of the subject 30 and the catheter (venous side) 16 carries out blood removal from the inside of the body of the subject 30.

The centrifugal pump 13 is referred to also as a centrifugal artificial heart. It drives a rotary body provided inside to give a pressure to the blood and circulate the blood in the circulation circuit. The motor 12 gives a rotational driving force to the rotary body of the centrifugal pump 13.

The oxygenator 14 carries out circulation of the blood and gas exchange of the blood (oxygen addition, carbon dioxide removal, and so forth). The oxygen supply source 15 is implemented by, e.g., an oxygen tank or the like and supplies oxygen to be added to the blood. The oxygen supplied from the oxygen supply source 15 is used at the time of gas exchange by the oxygenator 14.

The air bubble sensor 18 detects air bubbles flowing in the circulation circuit at the time of priming operation by a predetermined detection method (ultrasound, light, etc.). The blood filter 20 filters the blood and removes air bubbles in the blood.

The branching lines 19 switch the flow path of the circulation circuit. Specifically, in the case of extracorporeally circulating the blood of the subject 30, the branching lines 19 construct a circulation circuit passing through the inside of the body of the subject 30 to circulate the blood outside the body of the subject 30 as shown in FIG. 1A. At the time of priming operation, as shown in FIG. 1B, the routes of the circulation circuit to the inside of the body of the subject 30 are blocked by the branching lines 19 to construct a circulation circuit passing through only the outside of the body of the subject (in other words, circulation circuit that does not pass through the inside of the body of the subject 30). Furthermore, the inside of the circulation circuit is filled with a priming solution and the priming solution is circulated (without passing through the inside of the body of the subject). On the circulation circuit, one or plural air bubble expelling ports (not shown) for expelling air bubbles are made. By causing plural rounds of circulation of the priming solution in the circulation circuit, air bubbles in the circulation circuit are expelled from these air bubble expelling ports.

The control device 11 carries out overall control of operation in the extracorporeal circulation device 10. For example, the control device 11 gives a control signal to a drive circuit that controls the motor 12 to drive the centrifugal pump 13 and acquires an air bubble detection result (sensor value) from the air bubble sensor 18. Besides, in the control device 11, control of the priming operation and so forth are also carried out.

Here, a brief description will be made about the flow of treatment when the blood of the subject 30 is extracorporeally circulated by using the extracorporeal circulation device 10 shown in FIGS. 1A and 1B.

At the start of this treatment, the control device 11 controls execution of priming operation. At the time of the priming operation, the circulation circuit that does not pass through the inside of the body of the subject 30 is constructed by the branching lines 19 as shown in FIG. 1B. For example, at this time, a priming solution supply source 22 is connected to the branching lines 19 and a priming solution is supplied from this priming solution supply source 22 into the circulation circuit. This causes the inside of the circulation circuit to be filled with the priming solution.

Then, a drive signal is given to the motor 12 under control by the control device 11 and the centrifugal pump 13 is driven to provide a predetermined flow rate, so that plural rounds of circulation of the priming solution in the circulation circuit are caused. Air bubbles in the circulation circuit are expelled from the air bubble expelling ports and so forth along with this circulation. At this time, the air bubbles in the circulation circuit are detected by the air bubble sensor 18 and the control device 11 monitors the state of the air bubbles included in the circulation circuit based on the detection result by this air bubble sensor 18.

Here, when detecting that the air bubbles have been cleared off from the inside of the circulation circuit in accordance with a predetermined criterion (details of the predetermined criterion will be described later), the control device 11 ends the priming operation. At this end, the control device 11 notifies the user that the priming operation has ended by using a display unit (not shown), a speaker (not shown), or the like. The user who has received the notification of the end of the priming operation switches the branching lines 19 to reconfigure the circulation circuit so that it passes through the inside of the body of the subject 30 as shown in FIG. 1A. Then, the flow rate of blood is set and the centrifugal pump 13 is driven at the set blood flow rate to extracorporeally circulate the blood of the subject 30.

Upon the start of the extracorporeal circulation, the blood removed from the catheter (venous side) 16 passes through the centrifugal pump 13 to enter the oxygenator 14. In the oxygenator 14, treatment of gas exchange, i.e. oxygen addition, carbon dioxide removal, and so forth, is performed as described above. Thereafter, the blood passes through the blood filter 20 and so forth and the filtered blood is sent from the catheter (arterial side) 17 to the inside of the body of the subject 30. This treatment from blood removal to blood sending is repeatedly performed, so that the blood of the subject 30 is extracorporeally circulated.

The above is the description about one example of the overall configuration of the extracorporeal circulation device 10 relating to the present embodiment and the flow of treatment of extracorporeal circulation. Note that the configuration of the extracorporeal circulation device 10 shown in FIGS. 1A and 1B is absolutely one example and the configuration may be changed as appropriate. For example, a reservoir (blood is stored) may be provided.

2. Functional Configuration of Control Device

Next, the configuration of the control device 11 shown in FIG. 1A will be described by using FIG. 2.

The control device 11 has a main control unit (main controller) 100 that is responsible for control of the whole device, a timer unit 101, a storing unit 102, and a motor drive circuit 103 that applies a drive signal of the motor 12. Furthermore, the control device 11 has a display unit 105, an operation unit (i.e., operator interface) 106, a speaker 107, and the air bubble sensor 18 and they are connected to a system bus 120 via an interface 104. Moreover, the control device 11 has a sub-control unit 150 that is responsible for control of the whole of the control device 11 in place of the main control unit 100 if the main control unit 100 has stopped or has failed to normally function due to any cause.

The main control unit 100 is composed of CPU, ROM, and RAM similarly to a normal extracorporeal circulation device. Furthermore, the main control unit 100 and the sub-control unit 150 are connected by a signal line 131 for communicating with each other. In addition, in order to monitor whether the motor drive circuit 103 is outputting a signal corresponding to a blood flow rate set for the motor 12, the sub-control unit 150 is connected to a signal line 132 for receiving the drive signal. Note that, if the motor 12 is of such a type as to be driven by an applied voltage, an A/D converter for detecting the voltage is incorporated in the sub-control unit 150. Moreover, in the embodiment, if the main control unit 100 has become an abnormal state due to any cause, the sub-control unit 150 generates a control signal which is provided to main control unit 100 by a signal line 141 for completely stopping the main control unit 100.

3. Processing Procedures of Main and Sub-Control Units

First, the control device 11 in the embodiment suppresses increase in the complexity of the circuit scale and prevents increase in the power consumption with respect to existing devices. Furthermore, second, the control device 11 continues to make blood flow with the set amount of fluid sending per unit time even when the main control unit 100 falls into an abnormal state.

The above-described first task is realized by implementing the sub-control unit 150 in the embodiment by an FPGA (Field-Programmable Gate Array).

Furthermore, as for the second task, the following configuration is employed. Specifically, if the drive signal applied from the motor drive circuit 103 to the motor 12 of the centrifugal pump 13 does not fall within an allowable range commensurate with the set flow rate, the main control unit 100 is deemed to be in an abnormal state and the sub-control unit 150 takes over the role of it.

Further explanation will be unnecessary for those skilled in the art about the implementation by the FPGA for solving the above-described first task. Therefore, in the following, the processing procedures of the main control unit 100 and the sub-control unit 150 in the embodiment for solving the above-described second task will be described in more detail with reference to FIGS. 3 and 4.

FIG. 3 shows the processing procedure carried out by the main control unit 100 in the embodiment. A program relating to this diagram is stored in the storing unit 102.

Note that processing as shown is subsequent to reception of an instruction to start priming treatment from the operation unit 106.

First, the main control unit 100 notifies the sub-control unit 150 that the priming treatment is started via the signal line 131 in a step S101, and performs the priming treatment in a step S102. In the priming treatment, as described above, in the state in which the circulation circuit that does not pass through the inside of the body of the subject 30 has been constructed by the branching lines 19 as shown in FIG. 1B, a control signal to generate the drive signal for circulating a priming solution at a preset flow rate is output to the motor drive circuit 103. Because the circulation circuit is constructed outside the body of the subject 30, the motor drive circuit 103 at this time may set the flow rate by the centrifugal pump 13 to the maximum rate. The main control unit 100 continues the priming treatment until determining in a step S103 that the inside of the circulation circuit is filled with the priming solution and air bubbles have been expelled based on a signal from the air bubble sensor 18.

Then, if the main control unit 100 determines that air bubbles have been expelled from the circulation circuit, the processing proceeds to a step S104 and the main control unit 100 notifies the sub-control unit 150 that the priming treatment has been ended. Then, in the step S104, the main control unit 100 sets a blood flow rate $S_B$ to be used while blood is actually circulated. Upon the setting of the blood flow rate $S_B$, the main control unit 100 notifies the sub-control unit 150 of the set blood flow rate $S_B$ in a step S105.

Thereafter, the branching lines 19 are switched to make the configuration of FIG. 1A and, in a step S106, the main control unit 100 controls the motor drive circuit 103 so that the blood flow rate $S_B$ set from the operation unit 106 may be obtained, and performs extracorporeal circulation treatment. Then, the main control unit 100 repeats the processing of the step S106 until determining in a step S107 that an instruction to end the operation and stop the extracorporeal circulation has been made from the operation unit 106. If determining that the end instruction has been made, the main control unit 100 notifies the sub-control unit 150 that the blood circulation treatment has ended and ends the present processing.

Next, the processing procedure of the sub-control unit 150 in the embodiment will be described in accordance with a flowchart of FIG. 4. A program to execute the processing procedure relating to the flowchart of this diagram is stored in the sub-control unit (FPGA) 150.

First, in a step S201, the sub-control unit 150 waits for receiving a notification of the start of priming from the main control unit 100 (corresponding to S101 in FIG. 3). Upon receiving the notification of the start of priming treatment, the sub-control unit 150 detects a drive voltage signal applied to the motor 12 via the signal line 132 and detects its voltage level (for which A/D conversion is performed). Then, the sub-control unit 150 compares the detected voltage value V with an allowable range between upper and lower voltage values [$V_{PL}$, $V_{PH}$] at the time of the priming treatment and determines whether or not the following condition expression (1) is satisfied.

$$V_{PL} \leq V \leq V_{PH} \tag{1}$$

Then, if determining that the voltage value falls within this range, the sub-control unit 150 deems that the priming is being normally performed and waits for reception of a notification of the end of the priming.

If the main control unit 100 enters a state in which the above condition expression (1) is not satisfied before the notification of the end of the priming is received, the sub-control unit 150 deems the main control unit 100 to be in the stop or abnormal state due to any cause and the processing proceeds to a step S204. In the step S204, the sub-control unit 150 forcibly stops the main control unit 100 via the signal line 141 and assumes control of the display unit 105, the operation unit 106, the speaker 107, the air bubble sensor 18, the motor drive circuit 103, and so forth via various commands issued over system bus 120 by sub-control unit 150. Thereafter, the sub-control unit 150 takes over the processing of the priming treatment and the subsequent steps. Because the priming treatment and the subsequent steps are as already described by using FIG. 3, detailed description thereof is omitted.

On the other hand, if the notification of the end of the priming treatment is received (corresponding to S104 in FIG. 3) with the above condition expression (1) kept satisfied, the sub-control unit 150 forwards the processing to a step S206 and receives the blood flow rate $S_B$ set by a user from the main control unit 100 (corresponding to the step S105 in FIG. 3). Thereafter, in a step S207, the sub-control unit 150 decides an allowable range [$V_{BL}$, $V_{BH}$] of the drive voltage applied to the motor 12 for yielding the received blood flow rate $S_B$. For this decision, a lookup table in which the blood flow rates $S_B$ and the lower limit and upper limit values of the allowable drive voltage are stored may be stored in the sub-control unit 150 and the allowable range [$V_{BL}$, $V_{BH}$] may be derived with reference to it.

Thereafter, the processing proceeds to a step S208, where the sub-control unit 150 detects the drive voltage V to the motor 12 via the signal line 132 in the subsequent blood circulation treatment. Furthermore, the sub-control unit 150 determines whether or not the following condition expression (2) is satisfied and keeps on monitoring the progression of the blood circulation treatment with keeping of satisfaction of this condition expression (2).

$$V_{BL} \leq V \leq V_{BH} \tag{2}$$

If receiving a notification of end from the main control unit 100 with this state having been maintained (corresponding to the step S108 in FIG. 3), the sub-control unit 150 ends the present processing.

On the other hand, if the drive voltage V to the motor 12 via the signal line 132 does not satisfy the above condition expression (2) in the blood circulation treatment, i.e. if the drive signal outside the allowable range is applied (including also the case in which the applied voltage is zero), the sub-control unit 150 deems the main control unit 100 to be in the stop or abnormal state due to any cause and the processing proceeds to a step S210. In the step S210, the sub-control unit 150 forcibly stops the main control unit 100 via the signal line 141 and sets the display unit 105, the operation unit 106, the speaker 107, the air bubble sensor 18, the motor drive circuit 103, and so forth under control of the sub-control unit 150. Thereafter, the sub-control unit 150 takes over the blood circulation treatment. Because the blood circulation treatment is as already described by using FIG. 3, detailed description thereof is omitted.

As described above, according to the present embodiment, it becomes possible to configure an extracorporeal circulation device having high safety while suppressing increases in both the circuit scale and the power consumption.

The above is an example of a representative embodiment of the present invention. However, the present invention is not limited to the embodiment shown in the above description and the drawings and can be so carried out as to be modified as appropriate within such a range as not to change the gist thereof. In particular, in the embodiment, the configuration is so made that the centrifugal pump 13 monitors the voltage applied to its motor 12. However, if the motor 12 is of such a type as to be capable of changing the blood flow rate based on the number of pulses per unit time, it suffices to determine whether or not the number of pulses per unit time falls within an allowable range.

The present invention is not limited to the above-described embodiment and various changes and modifications are possible without departing from the gist and scope of the present invention. Therefore, the following claims are attached for determining the scope of the present invention.

The invention claimed is:

1. An extracorporeal circulation device that extracorporeally circulates blood of a subject by using a circulation circuit, the extracorporeal circulation device comprising:
a main control unit controlling the extracorporeal circulation device and a sub-control unit comprised of an FPGA (Field-Programmable Gate Array) configured to take over processing relating to extracorporeal circulation in place of the main control unit if the main control unit falls into an abnormal state,
wherein the main control unit includes an input connected to a signal line for receiving a control signal to stop the main control unit;
wherein the sub-control unit includes:
a monitoring circuit that monitors a drive signal applied by the main control unit to a motor of a pump for performing the extracorporeal circulation of the blood,
a decision circuit that determines whether the main control unit is in a normal state or is in an abnormal state by determining whether or not the drive signal falls within an allowable range for yielding a set amount of fluid sending per unit time during monitoring by the monitoring circuit, and
a control circuit that takes over and handles treatment relating to blood circulation in place of the main control unit if it is determined that the main control unit is in the abnormal state by the decision circuit,
wherein the control circuit is coupled to the signal line to send the control signal in order to forcibly stop the main control unit when the main control unit falls into the abnormal state.

2. The extracorporeal circulation device according to claim 1,
wherein the main control unit includes:
a notification circuit that notifies the sub-control unit of a start and an end of a period of priming treatment for the extracorporeal circulation device, and
wherein the sub-control unit includes:
a second decision circuit that determines whether or not the drive signal falls within a preset allowable range for the priming treatment from reception of a notification of priming start until reception of a notification of end, and
a second control circuit that takes over and handles the priming treatment in place of the main control unit if it is determined that the drive signal falls outside the allowable range by the second decision circuit,
wherein the second control circuit is coupled to the signal line to send the control signal in order to forcibly stop the main control unit when the drive signal falls outside the allowable range.

3. A control method of an extracorporeal circulation device having a main control unit that is responsible for control of the device and a sub-control unit that is configured by an FPGA (Field-Programmable Gate Array) and takes over processing relating to extracorporeal circulation in place of the main control unit if the main control unit falls into an abnormal state in order to extracorporeally circulate blood of a subject by using a circulation circuit, the control method comprising the steps of:
monitoring a drive signal applied to a motor of a pump for performing the extracorporeal circulation of the blood;
determining whether the main control unit is in a normal state or is in an abnormal state by determining whether or not the drive signal falls within an allowable range for yielding a set amount of fluid sending per unit time during monitoring by the monitoring step;
the sub-control unit forcibly stopping operation of the main control unit if it is determined that the main control unit is in an abnormal state in the determining step; and
the sub-control unit taking over treatment relating to blood circulation in place of the main control unit if it is determined that the main control unit is in an abnormal state in the determining step.

\* \* \* \* \*